United States Patent
Artzi et al.

(10) Patent No.: US 10,894,056 B2
(45) Date of Patent: Jan. 19, 2021

(54) PHOSPHOLIPID PREPARATIONS FOR THE IMPROVEMENT OF SLEEP

(71) Applicant: ENZYMOTEC LTD., Migdal Ha'emeq (IL)

(72) Inventors: Gali Olga Soria Artzi, Haifa (IL); Yael Richter, Kibutz Sarid (IL); Arnold W. Mech, Plano, TX (US)

(73) Assignee: ENZYMOTEC LTD, Migdal Haemeq (IL)

( * ) Notice: Subject to any disclaimer, the term of this patent is extended or adjusted under 35 U.S.C. 154(b) by 0 days.

(21) Appl. No.: 15/743,165

(22) PCT Filed: Jul. 11, 2016

(86) PCT No.: PCT/IB2016/001054
§ 371 (c)(1),
(2) Date: Jan. 9, 2018

(87) PCT Pub. No.: WO2017/009711
PCT Pub. Date: Jan. 19, 2017

(65) Prior Publication Data
US 2018/0243323 A1    Aug. 30, 2018

Related U.S. Application Data

(60) Provisional application No. 62/191,840, filed on Jul. 13, 2015.

(51) Int. Cl.
| | |
|---|---|
| A61K 31/685 | (2006.01) |
| A61P 25/00 | (2006.01) |
| A61K 31/23 | (2006.01) |
| A23D 7/01 | (2006.01) |
| A61K 31/202 | (2006.01) |
| A23L 33/12 | (2016.01) |
| A61K 31/201 | (2006.01) |
| A23D 9/013 | (2006.01) |

(52) U.S. Cl.
CPC .............. *A61K 31/685* (2013.01); *A23D 7/01* (2013.01); *A23D 9/013* (2013.01); *A23L 33/12* (2016.08); *A61K 31/201* (2013.01); *A61K 31/202* (2013.01); *A61K 31/23* (2013.01); *A61P 25/00* (2018.01); *A23V 2002/00* (2013.01)

(58) Field of Classification Search
None
See application file for complete search history.

(56) References Cited

FOREIGN PATENT DOCUMENTS

EP    2 263 695 A2    12/2010

*Primary Examiner* — Savitha M Rao
*Assistant Examiner* — Gregg Polansky
(74) *Attorney, Agent, or Firm* — Fox Rothschild LLP

(57) ABSTRACT

Phospholipid preparations for the improvement of sleep and/or treatment of sleep disorders. Methods of improving sleep and/or treating sleep disorders comprising administering the same.

19 Claims, No Drawings

PHOSPHOLIPID PREPARATIONS FOR THE IMPROVEMENT OF SLEEP

FIELD OF THE INVENTION

The invention relates to phospholipid preparations and uses thereof in improving sleep.

BACKGROUND OF THE INVENTION

Sleep plays a major role in children's and adults' well-being and is strongly influenced by health status, psychological stress and family issues as well as by multiple aspects of culture and environment.

Sleep may be divided into 2 main phases: non rapid eye movement (NREM) sleep which is subdivided into three sub-stages; and rapid eye movement (REM) sleep characterized by rapid eye movements, muscle atonia, and desynchronized EEG (Chokroverty et al., Indian J Med Res. 2010; 131:126-40).

When normal individuals first fall asleep, they enter Stage 1 (sleep drowsiness) and then progress through Stages 2 and 3 of NREM sleep. Stage 3, which represent deep sleep, may last a few minutes to an hour, depending on the person's age and other factors. Shortly after this, the first REM sleep period begins which lasts about 15-20 minutes and is followed by another non-REM cycle. This alternating pattern continues throughout the night (Goldstein & Walker, Annu Rev Clin Psychol. 2014; 10: 679-708). REM sleep comprises about 20 to 25 percent of total sleep in typical healthy adults (Phillips et al., J Theor Biol. 2013 21; 319:10).

Most dreams occur during REM sleep since there is activation of sensory systems during this period. The visual system is intensely activated, and all dreams have visual experiences. In addition, REM sleep stimulates the brain regions used in learning, emotion regulation and memory (Helm et al., Psychol Bull. 2009; 135(5):731-48).

The most important effect of REM deprivation is a dramatic shift in subsequent sleep patterns when the subject is again allowed to sleep without interruption. The longer the deprivation, the larger and longer the REM rebound, suggesting that REM sleep is physiologically necessary (Endo et al.). REM duration is also known to affect the sleep quality. A decrease in REM sleep significantly reduces sleep quality and increases sleep and fatigue complaints.

Sleep disorders are common and affect sleep quality and/or quantity. In certain cases, sleep disorders may lead to increased morbidity. Several epidemiological studies have clearly shown that sleep complaints are very common in the general population. Common findings in these complainers are insufficient sleep, sleep delay, fragmented sleep, and reduction in the percentage of REM sleep (Haba-Rubio, Dialogues Clin Neurosci. 2005; 7(4):335-46). These disorders may lead to problems falling asleep and staying asleep, difficulties staying awake or staying with a regular sleep/wake cycle, sleepwalking, bedwetting, nightmares, and other problems that interfere with sleep. Some sleep disorders can even be life-threatening.

Several types of treatments are used to treat patients with sleep disorders. Some of them directly address sleep issues and others address mental functions and stress reduction. Psychiatric medications like antidepressants are known to change sleep architecture by decreasing REM sleep and increasing stage 2 of sleep (Haba-Rubio, Dialogues Clin Neurosci. 2005; 7(4):335-46). Upon withdrawal of these medications REM sleep is increased. The effect of sleep medications like Benzodiazepines vary based on their duration of action; however, in general they decrease REM sleep while increasing total sleep time (Haba-Rubio, Dialogues Clin Neurosci. 2005; 7(4):335-46). The direct consequence of the decrement of REM sleep quantity is the worsening of sleep quality.

Omega-3 fatty acids were also tested for their effect on sleep. The omega-3 fatty acid Docosahexaenoic acid (DHA) was suggested to be more strongly correlated with sleep than other omega-3 fatty acids. Administration of relatively high doses (400-600 mg/day) of omega-3 fatty acids and specifically DHA, were found to have positive effect on sleep, i.e. increasing sleep duration and reducing the amount of sleep related problems (Lavialle et al., J. Nutr. 2008; 138:1719-24; see also Hansen et al., J Clin Sleep Med. 2014; 10(5):567-75, Huss et al., Lipids Health Dis. 2010; 9:105, and Montgomery et al., J Sleep Res. 2014; 23(4):364-88).

All in all it is suggested from the literature that many treatments for sleep disorders negatively affect REM sleep by decreasing its duration, thus resulting in deterioration of sleep quality (Pagel & Parnes, Prim Care Companion J Clin Psychiatry. 2001; 3(3):118-125).

SUMMARY OF THE INVENTION

The present invention provides a method for one or both of improving sleep in a subject and treating at least one sleep problem in a subject, comprising administering to the subject a preparation comprising an effective amount of a long chain poly unsaturated fatty acid (LC-PUFA) attached to a phosphatidylserine (PS).

The present invention also provides a preparation comprising an effective amount of a long chain poly unsaturated fatty acid (LC-PUFA) attached to a phosphatidylserine (PS), for use in one or both of improving sleep in a subject and treating at least one sleep problem in a subject.

The present invention also provides a preparation comprising an effective amount of a long chain poly unsaturated fatty acid (LC-PUFA) attached to a phosphatidylserine (PS), for use in a method for one or both of improving sleep in a subject and treating at least one sleep problem in a subject.

The present invention also provides a preparation comprising an effective amount of a long chain poly unsaturated fatty acid (LC-PUFA) attached to a phosphatidylserine (PS), for one or both of improving sleep in a subject and treating at least one sleep problem in a subject.

The present invention also provides a preparation comprising a long chain poly unsaturated fatty acid (LC-PUFA) attached to a phosphatidylserine (PS), for use in the manufacture of a pharmaceutical composition, nutritional composition, neutraceutical composition, functional food, or medical food, for one or both of improving sleep in a subject and treating at least one sleep problem in a subject.

In each of the above aspects of the present invention, the weight percentage of PS with respect to the preparation is at times greater than about 8%, 10%, 20%, or 28%, at times, greater than about 30%, 35%, or 38%, at times, greater than about 40%, 45%, 50%, 55%, 60% or 65%. At times, the content of LC-PUFA attached to the PS in the preparation out of the total fatty acids content attached to the PS in the preparation is greater than about 10%, at times, greater than about 20%, 28%, or 38%, at times greater than about 40%, 45%, 50%, 55% or 60%. At times, the EPA content attached to the PS in the preparation out of the total fatty acids content attached to the PS in the preparation is greater than about 5%, at times greater than about 10%, 20%, or 25%, at times greater than about 30%, 33%, 35% or 40%. At times the EPA content attached to the PS in the preparation out of the total fatty acids content attached to the PS in the preparation is greater than about 18% and lower than about 45%, at times greater than about 22% and lower than about 40%, at times greater than about 26% and lower than about 36%, and at times greater than about 27% and lower than about 34%. At times the Palmitic acid content attached to the PS in the preparation out of the total fatty acids content attached to the PS in the preparation is greater than about 14% and lower than about 42%, at times greater than about 18% and lower than about 40%, at times greater than about 20% and lower than about 30%, and at times greater than about 21% and lower than about 26%. At times, the DHA content attached to the PS in the preparation out of the total fatty acids content attached to the PS in the preparation is greater than about 6% and lower than about 25%, at times greater than about 8% and lower than about 22%, at times greater than about 11% and lower than about 20%, and at times greater than about 12% and lower than about 17%. At times, the Oleic acid content attached to the PS in the preparation out of the total fatty acids content attached to the PS in the preparation is greater than about 1% and lower than about 15%, at times greater than about 2% and lower than about 13%, at times greater than about 4% and lower than about 11%, and at times greater than about 5% and lower than about 8%. At times, the Linoleic acid content attached to the PS in the preparation out of the total fatty acids content attached to the PS in the preparation is greater than about 0.1% and lower than about 6.0%, at times greater than about 0.5% and lower than about 4.0%, at times greater than about 1.0% and lower than about 3.0%, or greater than about 1% and lower than about 2%, and at times greater than about 1.5% and lower than about 2.0%.

In the various aspects and embodiments of the invention the subject may by a human infant, a human toddler, a human child, a human adolescent, a human adult and a human geriatric subject.

In non-limiting embodiments of the present invention, the subject is a healthy infant, toddler, child, adolescent, adult or geriatric subject. In non-limiting embodiments of the present invention, the subject is a non-healthy infant, toddler, child, adolescent adult or geriatric subject. In non-limiting embodiments of the present invention, the non-healthy infant, toddler, child, adolescent, adult or geriatric subject suffers from one or more of a sleep disorder (e.g., fatigue, insufficient sleep duration or insufficient REM sleep), anxiety disorder, mood disorder, depression, obsessive compulsive disorder (OCD), drug dependence, post-traumatic stress disorder (PTSD), panic disorder, social phobia, predominant psychomotor disturbance, alcohol abuse, non-specific brain disorder, oppositional defiant disorder (ODD), attention deficit hyperactivity disorder (ADHD), ADHD symptoms, autism and epilepsy. In non-limiting embodiments of the present invention, the non-healthy toddler, child, adolescent, adult or geriatric subject is treated with non-stimulant medications.

The invention also provides a nutritional composition, pharmaceutical composition, nutraceutical composition, functional food, or medical food comprising a composition according to the invention for (or for use in or for use in a method for) one or both of improving sleep in a subject and treating at least one sleep problem in a subject.

In another one of its aspects the present invention provides a composition according to the invention for use in the preparation of a nutritional composition, pharmaceutical composition, nutraceutical composition, functional food, or medical food.

DETAILED DESCRIPTION OF THE INVENTION

The inventors of the present disclosure have found that specific lipid preparations improve sleep patterns, specifically, improve REM sleep and reduce fatigue symptoms. The preparations of the invention may also be useful in treating sleep disorders.

The present invention provides a method for one or both of improving sleep in a subject and treating at least one sleep problem in a subject, comprising administering to the subject a preparation comprising an effective amount of a long chain poly unsaturated fatty acid (LC-PUFA) attached to phosphatidylserine (PS).

The present invention also provides a preparation comprising an effective amount of a long chain poly unsaturated fatty acid (LC-PUFA) attached to phosphatidylserine (PS) for (or for use in or for use in a method for) one or both of improving sleep in a subject and treating at least one sleep problem in a subject.

The present invention also provides a method for one or both of improving sleep in a subject and treating at least one sleep problem in a subject, comprising administering to the subject a preparation comprising an effective amount of a long chain poly unsaturated fatty acid (LC-PUFA) attached to phosphatidylserine (PS), wherein the weight percentage of the PS with respect to the preparation is greater than about 8% and/or the content of LC-PUFA attached to the PS in the preparation out of the total fatty acids content attached to the PS in the preparation is greater than about 10%.

The present invention also provides a preparation comprising an effective amount of a long chain poly unsaturated fatty acid (LC-PUFA) attached to phosphatidylserine (PS) wherein the weight percentage of the PS with respect to the preparation is greater than about 8% and/or the content of LC-PUFA attached to the PS in the preparation out of the total fatty acids content attached to the PS in the preparation is greater than about 10% for (or for use in or for use in a method for) one or both of improving sleep in a subject and treating at least one sleep problem in a subject.

The present invention also provides a method for one or both of improving sleep in a subject and treating at least one sleep problem in a subject, comprising administering to the subject a preparation comprising an effective amount of EPA attached to phosphatidylserine (PS), wherein the weight percentage of the PS with respect to the preparation is greater than about 8% and/or the content of EPA attached to the PS in the preparation out of the total fatty acids content attached to the PS in the preparation is greater than about 5%.

The present invention also provides a preparation comprising an effective amount of a long chain poly unsaturated fatty acid (LC-PUFA) attached to phosphatidylserine (PS) wherein the weight percentage of the PS with respect to the preparation is greater than about 8% and/or the content of EPA attached to the PS in the preparation out of the total fatty acids content attached to the PS in the preparation is greater than about 5% for (or for use in or for use in a method for) one or both of improving sleep in a subject and treating at least one sleep problem in a subject. The invention also provides a method for one or both of improving sleep in a subject and treating at least one sleep problem in a subject, comprising administering to the subject a preparation comprising an effective amount of a long chain poly unsaturated fatty acid (LC-PUFA) attached to a phosphatidylserine (PS), wherein the weight percentage of the PS with respect to the preparation is greater than about 8% and out of the total fatty acids content attached to the PS in the preparation the content of EPA attached to the PS in the preparation is greater than about 5%, the content of palmitic acid attached to the PS in the preparation is greater than about 14% and lower than about 42%, the content of DHA attached to the PS in the preparation is greater than about 6% and lower than about 25%, the content of oleic acid attached to the PS in the preparation is greater than about 1% and lower than about 15%, and the content of linoleic acid attached to the PS in the preparation is greater than about 0.1% and lower than about 6%.

The present invention also provides a preparation comprising an effective amount of a long chain poly unsaturated fatty acid (LC-PUFA) attached to phosphatidylserine (PS) wherein the weight percentage of the PS with respect to the preparation is greater than about 8% and out of the total fatty acids content attached to the PS in the preparation the content of EPA attached to the PS in the preparation is greater than about 5%, the content of palmitic acid attached to the PS in the preparation is greater than about 14% and lower than about 42%, the content of DHA attached to the PS in the preparation is greater than about 6% and lower than about 25%, the content of oleic acid attached to the PS in the preparation is greater than about 1% and lower than about 15%, and the content of linoleic acid attached to the PS in the preparation is greater than about 0.1% and lower than about 6%, for (or for use in or for use in a method for) one or both of improving sleep in a subject and treating at least one sleep problem in a subject.

The invention also provides a method for one or both of improving sleep in a subject and treating at least one sleep problem in a subject, comprising administering to the subject a preparation comprising an effective amount of a long chain poly unsaturated fatty acid (LC-PUFA) attached to a phosphatidylserine (PS), wherein the weight percentage of the PS with respect to the preparation is greater than about 40% and out of the total fatty acids content attached to the PS in the preparation the content of EPA attached to the PS in the preparation is greater than about 25%, the content of palmitic acid attached to the PS in the preparation is greater than about 21% and lower than about 26%, the content of DHA attached to the PS in the preparation is greater than about 12% and lower than about 17%, the content of oleic acid attached to the PS in the preparation is greater than about 5% and lower than about 8%, and the content of linoleic acid attached to the PS in the preparation is greater than about 1% and lower than about 2%.

The present invention also provides a preparation comprising an effective amount of a long chain poly unsaturated fatty acid (LC-PUFA) attached to phosphatidylserine (PS) wherein the weight percentage of the PS with respect to the preparation is greater than about 40% and out of the total fatty acids content attached to the PS in the preparation the content of EPA attached to the PS in the preparation is greater than about 25%, the content of palmitic acid attached to the PS in the preparation is greater than about 21% and lower than about 26%, the content of DHA attached to the PS in the preparation is greater than about 12% and lower than about 17%, the content of oleic acid attached to the PS in the preparation is greater than about 5% and lower than about 8%, and the content of linoleic acid attached to the PS in the preparation is greater than about 1% and lower than about 2%, for (or for use in or for use in a method for) one or both of improving sleep in a subject and treating at least one sleep problem in a subject.

The term "improving sleep" or any lingual variations thereof as used herein should be understood to encompass improvement of at least one sleep parameter. Non-limiting examples of such improvements are: improving sleep patterns, improving sleep maturation, improving rapid eye movement (REM) sleep, improving non-REM sleep, improving sleep quality, improving night sleep quality, improving sleep latency, increasing sleep duration, increasing night sleep duration, regulation of sleep, normalization of sleep e.g., normalization of sleep hours (as recommended for each age group of subjects e.g., infants) normalization of wake, reduce number of awakenings during sleep, improving continued sleep, improving restful sleep, reducing fatigue symptoms, regulation of circadian rhythm, improving effectiveness of sleep, and reducing night awaking. At times, the term is to be envisaged as optimizing at least one sleep related parameter.

As used herein, the term "increase sleep duration" or any lingual variations thereof is to be envisaged as any one of, but not limited to, increasing the time duration of a single sleeping episode, increasing accumulated sleeping time during the whole day (out of 24 hours) and increasing accumulated sleeping time during the night.

The term "sleep problem" or any lingual variations thereof as used herein should be understood to encompass a sleep disturbance, an abnormal sleep related condition, or a sleep disorder. Non-limiting examples of sleep problems include fatigue, insufficient REM sleep, REM Sleep behavior disorder, Stimulant-Dependent Sleep Disorder, Alcohol-Dependent Sleep Disorder, reduced sleeping hours (in comparison with accepted norms e.g., for a specific group of subjects such as infants at different ages), insufficient sleep duration, dyssomnias, parasomnias, sleep-onset difficulties, limit-setting sleep disorder, insufficient sleep syndrome, snoring, obstructive sleep apnea (OSA), sleepwalking, sleeplessness, insomnia, night terrors, nightmares, bedwetting, rhythmic movement disorders (such as head banging or rocking), restless leg syndrome, circadian rhythm disorders such as jet lag, shift work sleep disorder, delayed sleep phase, advanced sleep phase, non-24-hour sleep wake disorder, nocturnal sleep disturbance, awakening several times during the night, excessive tiredness related symptoms, problems falling asleep, problems remaining asleep, problems of experiencing restful sleep, and irregular sleep-wake rhythm.

As used herein, the term "insufficient sleep duration" or any lingual variations thereof is to be envisaged as any one of, but not limited to, insufficient time duration of a single sleeping episode, insufficient accumulated sleeping time during the whole day (out of 24 hours) and insufficient accumulated sleeping time during the night compared for example to acceptable norms at the specific subject's gender and/or age and/or weight and/or health condition.

In the context of the present invention the term "treatment" or "treating" and the like are used herein to refer to obtaining a desired pharmacological or physiological effect on the subject, including prophylactic in terms of "preventing" or partially preventing an undesired condition or symptoms from developing and/or therapeutic in terms of "curing" partial or complete curing of an already existing undesired condition and/or ameliorating, controlling, or managing the undesired symptoms. The term "treating" is used within the context of the present disclosure as treatment of subjects who are healthy and/or suffer from a disorder, disease, or impaired physiological/medical sleep related condition. At times treating may be of a subject which may be one at risk for developing an undesired condition that may affect sleep.

Improvement of sleep parameters may be measured by quantity and/or quality means.

As used herein, the term "subject" refers to a healthy subject or a subject suffering from a specific disorder/condition or at risk of developing a specific disorder/condition. It is noted that the disorder and/or condition may or may not be related to a sleep problem. Thus, at times, the sleep problem may be a side effect associated with a specific disorder and/or condition.

In some embodiments according to the invention the subject may be a subject at risk of developing a sleep problem. A subject at risk of developing a sleep problem may be, but is not limited to any one of: a preterm infant (born prematurely); a small for gestation age infant; a subject with poor sleeping patterns; children born prematurely; infants born by Caesarean section; infants suffering from colic; infants with feeding intolerance and abdominal pain or irritability; infants that need medical attention; infants with airway abnormalities; infants with breathing difficulties caused by gastroesophageal reflux or enlarged adenoids; a subject suffering from an endocrine malfunction (hormones); a subject suffering from a chronic illness; a subject with intrauterine sleep retardation or Intrauterine Growth Retardation (IUGR); a subject suffering from failure to thrive and/or inadequate weight gain any time after birth; a subject consuming drugs that may affect sleep habits; a subject with Attention Deficit Hyperactivity Disorder (ADHD), a subject suffering from anxiety disorder, a subject suffering from mood disorder, a subject suffering from depression, a subject suffering from obsessive compulsive disorder (OCD), a subject suffering from drug dependence, a subject suffering from post-traumatic stress disorder (PTSD), a subject suffering from panic disorder, a subject suffering from social phobia, a subject suffering from predominant psychomotor disturbance, a subject suffering from alcohol abuse, a subject suffering from non-specific brain disorder, a subject suffering from oppositional defiant disorder (ODD), a subject with breathing disorders; a subject with dementia; a subject suffering from depression; a subject with Chronic obstructive pulmonary disease (COPD); a subject suffering from epilepsy; a subject suffering from pain, etc.

In the various aspects and embodiments of the invention the subject may by a human infant, a human toddler, a human child, an adolescent, an adult and a geriatric subject.

In some embodiments according to the invention the subject may or may not suffer from medical problems that may interfere with sleep. In some embodiments according to the invention the subject may be any one of an infant (preterm or term, newborn from the day of birth, to age of about 12 months i.e., about 1 year), a toddler (from about one year up to about the age of 3), a child (from about 3 years to about 12 years), an adolescent (from 12 years to about 18 years), an adult (over 18 years). At times the subject may be a geriatric subject.

In some embodiments of the invention the infant may be any one of pre-term infant and term infant; a small for gestation age (SGA) infant; an appropriate for gestation age (AGA) infant; large for gestation age (LGA) infant; an infant born by regular (vaginal) delivery, cesarean surgery (Caesarean section) or any other modes of delivery. As used herein, the term "newborn" includes pre-mature infants, post-mature infants and full term newborns.

According to embodiments of the present invention the subject may be a human adult.

According to embodiments of the present invention, the lipid preparation may be provided to the subject for a period of time from day one to weeks, months, etc.

According to embodiments of the present invention the subject may be a healthy subject experiencing sleep problem/s such as for example reduced sleeping hours (e.g., insufficient sleep such as insufficient night sleep duration). The subject may also be a non-healthy subject experiencing sleep problem/s such as for example reduced sleeping hours (e.g., insufficient sleep like insufficient night sleep duration). The subject may also be a non-healthy subject suffering from ADHD symptoms, autism or epilepsy. The subject may also be a non-healthy subject suffering from one or more of anxiety disorder, mood disorder, depression, obsessive compulsive disorder (OCD), drug dependence, post-traumatic stress disorder (PTSD), panic disorder, social phobia, predominant psychomotor disturbance, alcohol abuse, non-specific brain disorder, oppositional defiant disorder (ODD) and attention deficit hyperactivity disorder (ADHD). The subject may be treated with non-stimulant medications.

The present invention provides a pharmaceutical composition, nutritional composition, nutraceutical composition, functional food, or medical food comprising a preparation comprising LC-PUFA attached to phosphatidylserine (PS), wherein the weight percentage of the PS with respect to the preparation is greater than about 8%.

Thus the preparation according to the invention may be used in the preparation of or as part of a pharmaceutical composition, nutritional composition, nutraceutical composition, functional food, or medical food.

In some embodiments the preparation according to the invention may be used in the preparation of medical food.

In a further one of its aspects the present invention provides a medical food comprising a preparation according to the invention for use in a method for one or both of improving sleep in a subject and treating at least one sleep problem in a subject.

A nutritional composition as used herein can be any nutritional composition including, but not limited to: human milk fat substitute, formula, infant formula, toddler formula, child formula, adult formula, dairy product including milk and dairy drinks, milk powder, drinks, shakes, ice cream, biscuit, soy product, bakery, pastry, bread, cake, sauce, soup, prepared food, including prepared mashed vegetables and/or fruits, frozen food, condiment, confectionary, oil, fat, margarine, spread, filling, meat product, cereal, instant product, instant drink product, infant food, toddler food, bar, snack, candy, and chocolate product.

A functional food as used herein can be any functional food, including, but not limited to: dairy product, ice-cream, biscuit, soy product, bakery, pastry, cakes and bread, instant product, sauce, soup, prepared food, frozen food, condiment, confectionary, oils and fat, margarine, spread, filling, cereal, instant product, drinks and shake, infant food, bar, snack, candy, and chocolate product.

A nutraceutical composition as used herein can be any nutraceutical, which can be any substance that may be considered as a food or part of a food and provides medical or health benefits, including the prevention and treatment of diseases or disorders. Such nutraceutical compositions include, but are not limited to: a food additive, a food supplement, a dietary supplement, genetically engineered foods (such as for example vegetables, herbal products, and processed foods such as cereals, soups, and beverages), stimulant functional food, clinical nutrition product, medical food, and pharmafood. Dietary supplements may be delivered in the form of soft gel capsules, tablets, syrups, and other known dietary supplement delivery systems.

The pharmaceutical or nutraceutical compositions may be in any of the many dosage delivery forms commonly used in the art. Pharmaceutical compositions suitable for oral administration may be presented as discrete dosage units (such as pills, tablets, pellets, dragées, capsules, or softgel), as a powder or granule, or as a solution, suspension, syrup, or elixir.

A medical food as used herein is specially formulated and intended for the dietary management of a disease/disorder that has distinctive nutritional needs that cannot be met by normal diet alone.

Suitable routes of administration for the compositions of the subject invention are oral, nasal, intranasal, inhalation, buccal, sublingual administration, administration via a feeding tube, topical, transdermal, or parenteral (including subcutaneous, intramuscular, intravenous and intradermal) administration. In an embodiment, the compounds and preparations are administered orally.

Administration is usually via oral or enteral route, which may include the use of gavage feeding, with a gastric feeding tube, sonda, particularly where adapted for preterm infant feeding, infant feeding or for clinical nutrition.

According to another embodiment, a daily dose of the preparation of the invention as described herein optionally provides 75-600 mg PS to the subject, at times 75-450 mg PS, at times 75-300 mg PS, at times 75-225 mg PS and at times 75-150 mg PS or 110-450 mg PS. The daily dose may optionally be divided to a plurality of doses each day or alternatively may optionally be delivered as a single bolus each day.

According to another embodiment, a daily dose of the preparation of the invention as described herein optionally provides 20-172 mg EPA to the subject, at times 21.5-129 mg EPA, at times 21.5-86 mg EPA and at times 21.5-43 mg EPA or 32-130 mg EPA. The daily dose may optionally be divided to a plurality of doses each day or alternatively may optionally be delivered as a single bolus each day.

According to another embodiment, a daily dose of the preparation of the invention as described herein optionally provides 8-68 mg DHA to the subject, at times 8-51 mg DHA, at times 8-34 mg DHA and at times 8.5-17 mg DHA or 12-51 mg DHA. The daily dose may optionally be divided to a plurality of doses each day or alternatively may optionally be delivered as a single bolus each day.

The daily dose according to at least some embodiments of the present invention, when administrated as capsules, tablets, syrups, gummies, and other known delivery systems, optionally comprises one, two, three, four, five, six, seven or eight delivery units per day.

It should be noted that the preparation of the invention may also comprise other phospholipids, such as phosphatidylcholine (PC), phosphatidylethanolamine (PE), phosphatidyl-inositol (PI), phosphatidylglycerol (PG) and phosphatidic acid (PA), to which fatty acid acyls are covalently attached (bonded) at either or both of the sn-1 or sn-2 positions of the glycerol moiety of the phospholipid. The fatty acid conjugation profile of any of the above-noted polar lipids may be the same as, or different from, the fatty acid conjugation profile of PS, as disclosed herein.

According to an embodiment the weight percentage of phosphatidylcholine (PC) with respect to the preparation is less than 5% or 4%, at times less than 3.5% or 3%, at times less than 2.5% or 2% and at times less than 1.5%, 1% or 0.5%.

According to an embodiment the weight percentage of ether phosphatidylserine with respect to the preparation is below 20%, at times below 15%, at times below 10%, at times above 1% and below 9%, at times above 2% and below 8%, at times above 3% and below 7% and at times above 4% and below 6%.

The terms "glycerophospholipid" and "phospholipids" are used herein interchangeably and should be understood to encompass a lipid of the general formula:

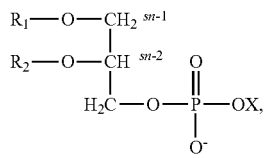

wherein X represents a moiety selected from serine, choline, ethanolamine, inositol, glycerol and hydrogen, and $R_1$ and $R_2$, which may be identical or different, independently represent hydrogen or an acyl group, wherein said acyl group is selected from saturated, mono-unsaturated or poly-unsaturated acyl groups (PUFA). The sn-1 and sn-2 positions as used herein and as indicated in the above formula, refer to the respective carbon atoms on the glycerol backbone wherein $R_1$ and $R_2$, are hydrogen or acyl groups substituted on the corresponding position.

The term "lysophosphatidic acid" is used herein when X represents hydrogen and one of $R_1$ or $R_2$ is Hydrogen as well.

As described herein, the terms "substituted," "conjugated, ", and "attached" are used interchangeably and should be understood to encompass a fatty acid acyl covalently attached to the glycerophospholipid backbone of a phospholipid of the invention. As noted above, the fatty acid may be attached to the sn-1 and/or sn-2 positions.

As used herein, the term "fatty acid" should be understood to encompass a carboxylic acid with a long unbranched aliphatic tail (chain), which is either saturated, or unsaturated having one unsaturated bond (mono-unsaturated fatty acids) or two or more unsaturated bonds (poly-unsaturated fatty acids). When referring to a "fatty acid acyl" it should be understood to encompass an —C(=O)—R radical wherein R is a long unbranched aliphatic tail, which is either saturated or unsaturated having one unsaturated bond (mono-unsaturated fatty acids) or two or more unsaturated bonds (poly-unsaturated fatty acids).

As used herein, the term ω-X, Omega-X, n-X (X denotes a number), are interchangeably used and should be understood to denote the carbon atom furthest from the carboxyl group of a fatty acid.

Non-limiting examples of saturated fatty acids include: Butyric acid (Butanoic acid, C4:0), Caproic acid (Hexanoic acid, C6:0), Caprylic acid (Octanoic acid, C8:0), Capric acid (Decanoic acid, C10:0), Lauric acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidic acid (Eicosanoic acid, C20:0), Behenic acid (Docosanoic acid C22:0).

Non-limiting examples of unsaturated fatty acids include: Myristoleic acid (C14:1, ω-5), Palmitoleic acid (C16:1, ω-7), Oleic acid (C18:1, ω-9), Linoleic acid (C18:2, ω-6), Linolenic acid (C18:3) [Alpha-linolenic acid (C18:3, ω-3), Gamma-linolenic acid (C18:3, ω-6)], Eicosenoic acid (C20:1, ω-9), Arachidonic acid (C20:4, ω-6), Eicosapentaenoic acid (C20:5, ω-3), Erucic acid (C22:1, ω-9), Docosapentanoic acid (C22:5, ω-3) and Docosahexaenoic acid (C22:6, ω-3), Nervonic acid (C24:1, ω-9).

The term a "[fatty acid] conjugated to phospholipid," should be understood to encompass a phospholipid wherein a fatty acid acyl is conjugated at position sn-1 and/or position sn-2 of the phospholipid backbone (through the glycerol oxygen atom). In one embodiment, a fatty acid is conjugated at position sn-1, and position sn-2 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-1. In another embodiment, a fatty acid is conjugated at position sn-2 and position sn-1 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-2.

The term phosphatidylserine is often also referred to in the literature as serine glycerophospholipid, phosphatidyl serine, and PS.

A preparation of the invention may also be administered in conjunction with other compounds, including, but not limited to folic acid, vitamins, minerals, amino acids, nucleotides, antioxidants and so forth.

It will be appreciated that a preparation of the invention may be combined with other treatment methods known in the art. Thus, treatment of sleeping problems using a preparation or product of the invention may optionally be combined with conventional therapies for sleeping problems.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising," will be understood to imply the inclusion of a stated integer or step or group of integers or steps but not the exclusion of any other integer or step or group of integers or steps.

Further, all numerical values, e.g. when referring the amounts or ranges of the elements constituting the various lipid compositions herein are approximations which are varied (+) or (−) by up to 20%, at times by up to 10% of the stated values. It is to be understood, even if not always explicitly stated that all numerical designations are preceded by the term "about".

A preparation as described herein may be optionally prepared through enzymatic, chemical or molecular biology methods. Briefly, a phospholipid mixture can be enriched with the required fatty acids (e.g. EPA, Palmitic acid, DHA, oleic acid, linoleic acid) by enzymatic processes, e.g. enrichment of a natural phospholipid with specific fatty acids by enzymatic transesterification/esterification. Another pathway to acquire the preparation is to obtain a phospholipid source which is naturally rich in the required fatty acids, such as marine-derived lecithin (e.g. krill, fish, algae, and squid) or eggs phospholipids. Usually, in order to obtain the recited ratio between the different phospholipids in the mixture, transformation of the phospholipid head group to serine (using PLD enzymes) may be required to obtain PS. Such methods have been described in WO 2005/038037. Alternatively, the phospholipid mixture, according to at least some embodiments of the present invention can be prepared by GMO (genetically modified organisms)/biotechnology methods, for example, providing phospholipids-producing organisms with the required fatty acids to obtain the different phospholipids conjugates.

According to another embodiment of the present invention, the preparation is preferably prepared from a natural, synthetic or semi-synthetic source or any combinations thereof. In an embodiment of the present invention, said natural source is derived from any one of plant (such as for example soy and algae), non-mammalian animal (such as for example krill, fish (such as for example Herring and blue Whiting), or microorganism (such as for example bacteria) source or any combinations thereof. In yet a further embodiment, the production of said lipid preparation involves an enzymatic catalysis.

Quantification of Phospholipids by $^{31}$P-NMR Spectroscopy Using the Internal Standard Method Purpose: This method is used to determine the phospholipid content by weight in the preparation. Instruments: Bruker Avance III 600 MHz with automatic sample changer and cQNP probe head. Bruker Avance 300 MHz with automatic sample changer and BBI probe head. For the quantification of phospholipids in the preparation of the invention (powder form) approximately 300 mg of the test substance and 20 mg of internal standard TPP (triphenylphosphate) is dissolved in 1.5 ml CDCl$_3$, 3 ml methanol and 3 ml aqueous Cs-EDTA solution (0.2 m, pH 7.5). After 15 minutes of shaking, the organic layer is separated by centrifugation and measured with $^{31}$P-NMR. The integrated signals of the test substance and of the internal standard TPP (triphenylphosphate) are used for calculation. The ratio of integrals corresponds to the molar ratio of the compared substances. For calculation software Microsoft Excel 14.0 is used.

Calculation:

$$MOL_{IS}[\text{mMol}] = \frac{W_{IS}[\text{mg}] * C_{IS}[\%]}{MW_{IS}[\text{g/Mol}] * 100} \quad \text{Equation 1}$$

$$MOL_P[\text{mMol}] = \frac{I_P * H_{IS} * MOL_{IS}[\text{mMol}]}{I_{IS} * H_P} \quad \text{Equation 2}$$

$$weight-\%_P = \frac{MW_P[\text{g/Mol}] * MOL_P[\text{mMol}] * 100}{W_P[\text{mg}]} \quad \text{Equation 3}$$

Declaration of Variables:

|  | test substance | internal standard |
|---|---|---|
| molecular weight | $MW_P$ (According to the MW table presented below) | $MW_{IS}$ |
| initial weight [mg] | $W_P$ | $W_{IS}$ |
| content [%-by weight] | weight-$\%_P$ | $C_{IS}$ |
| Mol [mMol] | $MOL_P$ | $MOL_{IS}$ |
| integral | $I_P$ | $I_{IS}$ |
| number of P-atoms | $H_P$ | $H_{IS}$ |

-continued

| Phospholipid | MW (g/mol) |
|---|---|
| Phosphatidylcholine (PC) | 812.0 |
| Lyso Phosphatidylcholine (LPC) | 534.5 |
| Phosphatidylinositol (PI) | 907.0 |
| Lyso Phosphatidylinositol (LPI) | 629.5 |
| Phosphatidylserine (PS) | 833.0 |
| Lyso Phosphatidylserine (LPS) | 555.5 |
| Phosphatidyl Ethanolamine (PE) | 770.0 |
| Lyso Phosphatidyl Ethanolamine (LPE) | 492.5 |
| Phosphatidic Acid (PA) | 746.0 |
| Lyso Phosphatidic Acid (LPA) | 468.5 |
| Acyl Phosphatidyl Ethanolamine (APE) | 1032.0 |
| Other | 812.0 |

Determination of Fatty Acid Percentage in Phospholipids

Purpose: This method is used to determine the percentage of a fatty acid attached to PS in the preparation with respect to the total fatty acid content attached to the PS in the preparation.

Materials: Acetic acid glacial A.R., Methanol abs. A.R., Chloroform A.R., Acetone A.R., Hexane A.R., Toluene A.R., Di-isopropyl ether AR., Butylhydroxytoluene, Sigma Lot #W218405 or equivalent, Sodium Sulfate Anhydrous, Sigma, Lot #31481, or equivalent, Sodium methoxide 25% (w/w) in methanol, Sigma Cat #15625-6, or equivalent, Primuline, Sigma Cat #206865, or equivalent, GC reference standard, Nuchek Lot #566B, Phosphatidylcholine reference standard, Sigma Aldrich Lot Cat #P3556, or equivalent, Phosphatidylserine reference standard, Sigma Aldrich Lot Cat #P5660, or equivalent, TLC Plates 20×10, silica gel 60 F254 layer MERCK 1.05715, or equivalent.

Apparatus: Orbital shaker with temperature control, Analytical Balance, Pipettor 0.2-1 ml and 1-5 ml range, Volumetric pipette 10 ml class A, TLC tank, suitable for 20×10 TLC plates, Disposable capillaries 5 µl volume, GC systems suitable for use with capillary column, equipped with oven capable of maintaining temperature with +0.1 C degree accuracy, FID detector, split mode injection unit with temperature controller, GC capillary column, G16 USP phase, length 30 m, I.D. 0.25 mm, film 0.25 µm, or similar.

Reagents and Solutions Preparation:

Sodium Methoxide solution: Accurately weigh 54 g of Sodium methoxide 25% into a 500 ml volumetric flask. Dilute to volume with Methanol Abs. Store in a dark place, in a tightly closed glass container. Solution is stable for up to 3 months.

Chloroform:Methanol 95:5 solution: Mix 95 volumes of Chloroform with 5 volumes of Methanol. Store in a dark place, in a tightly closed glass container. Solution is stable for up to one year.

Developing solution: Mix Water, Methanol, Acetic acid, Acetone and Chloroform in a volume ratio of 5:10:15:20:50, respectively. Store in a dark place, in a tightly closed glass container. Solution is stable for up to one year.

Primuline solution: Weight 10 mg into a 100 ml volumetric flask. Add 60 ml Acetone and 40 ml water. Mix well. Store in a dark place, in a tightly closed glass container. Solution is stable for up to one year.

Antioxidant solution 1 mg/ml: Weighed 25±2 mg Butylhydroxytoluene into a 25 ml volumetric flask. Add Toluene to the Mark, mix well (This solution can be kept for 3 month at room temperature.).

Antioxidant solution 0.05 mg/ml: Pipette 10 ml of the above solution into a 200 ml volumetric flask, add Toluene to the Mark, mix well. Store at 50° C. for up to 3 months. (This solution can be kept for 3 months at room temperature).

PS/PC mix standard solution: Add about 20 mg of Phosphatidylserine reference standard into a 2 ml volumetric flask, add about 20 mg of Phosphatidylcholine reference standard. Add a small amount of Chloroform:Methanol solution sufficient to dissolve the reference standards. Once dissolved fill up to volume with the same Chloroform:Methanol solution. Store in a tightly closed container at −20° C. Stable for up to 3 months.

System suitability solution: Empty an ampoule containing 100 mg of GC reference standard 566B into a 50 ml volumetric flask, add 0.05 mg/ml Antioxidant Solution 0.05 mg/ml to the Mark. Mix well. Store in tightly closed container at −20° C. Stable for up to 3 months.

Procedure: Sample solution preparation: Accurately weight 500 mg of the sample into a 20 ml vial with ground stopper. Add 10 ml Chloroform: Methanol solution and shake vigorously for 2-3 minutes.

Phospholipids purification: Perform test in duplicate. Perform blank determination by developing an unloaded plate (no sample applied to the plate). Sample silica from an area corresponding to the area of the sample followed by methylation as described above. Apply an even thin band of 120 µl sample solution on TLC plate, 1 cm above the plate bottom, leaving a 3 cm margin on each side. At one of the margins, apply PS/PC mix standard solution of approximately 5 µl, spot wise by means of a disposable capillary. Add 45 ml of di-isopropyl ether to the 20×10 mm Glass TLC chamber. Saturate the chamber for 15-20 minutes. Develop TLC plate up to about 90 mm mark. Dry the plate in fume hood under air at room temperature for about 10 minutes. Repeat the previous two steps once more using the same chamber. Add 45 ml of developing solution to the 20×10 mm Glass TLC chamber. Saturate the chamber for 15-20 minutes. Develop TLC plate up to about 80 mm mark. Dry the plate in fume hood under a current of air at room temperature for about 10 minutes. Spray the TLC plate evenly with Primuline solution and dry under a current of air at room temperature for about 10 minutes. Place the plate under UV lamp at 365 nm to observe the bands. Identify the corresponding bands using spots of PS mix reference standard and scrub the bands in-to a 20 ml glass vial with ground stopper.

Methylation: To the 20 ml vials containing scrubbed silica add 2 ml Toluene. Then add 4 ml of Sodium methoxide solution. Shake for 15 minutes at 50° C. Then add 200 µl of Acetic acid and 4 ml of purified water, shake vigorously for 1 minute. Add 2 ml of Hexane and shake vigorously for 30 seconds. Transfer only the upper organic layer to a 20 ml bottle. Again add 2 ml of Hexane and shake vigorously for 30 seconds. Transfer only the upper organic layer to the same 20 ml bottle. Combine organic phases and dry over 0.5 grams Sodium sulfate. Filter through a 0.2 micron filter. Evaporate hexane under a nitrogen stream, until a volume of about 0.5 ml is reached. Analyze the sample by Gas Chromatography.

Gas Chromatography Settings:

| Column | Capillary column, G16 USP phase, length 30 m, I.D. 0.25 mm, film 0.25 μm, or similar |
|---|---|
| Carrier gas | Helium |
| Equilibration time | 2 min |

| Temperatures | Initial Temp. | Initial Time | First Temp. rate | Final Temp. | Hold Time |
|---|---|---|---|---|---|
| | 170° C. | 2 min | 1° C./min | 210° C. | 2 min |
| | | | Second Temp. rate | Final Temp. | Hold Time |
| | | | 30° C./min | 240° C. | 11 min |

| Injector temp. | 250° C. |
|---|---|
| Pressure | 21 psi |
| Split ratio | 25:1 |
| Helium flow | 1.5 ml/min (constant flow) |
| Total flow | 41.4 ml/min |
| Detector temp. | 270° C. |
| Hydrogen flow | 40 ml/min |
| Air flow | 400 ml/min |
| Injection volume | 1 μl |

Note:
Gas flow and temperature ramp may be adjusted to meet system suitability acceptance criteria.

Chromatography Injection Order: First inject Hexane and insure that there is no response in the relevant retention time. Next, inject System Suitability solution. The acceptance criteria is as follows: the resolution (R) between the peaks due to methyl oleate (C18:1n9) and methyl cis-vaccinate (C:181n11)≥1.3.

$$\text{resolution } R = \frac{2(t2 - t1)}{1.7(W1 + W2)}$$

where, t1 and t2 are the retention times of the two components and W1 and W2 are the corresponding widths at half-height of the peaks. Next, inject sample from blank TLC plate (TLC blank). If there are peaks observed in the TLC blank chromatogram (except the solvent peak), they must be subtracted from the chromatogram of the sample. Finally, inject Samples.

Calculation: Calculate the area percentage of a fatty acid component in sample by the formula: % FA=AreaFA/AreaTot, where AreaFA is the area of the peak response obtained for an individual fatty acid methyl ester and AreaTot is the sum of the peak areas of all of the peaks, corresponding to fatty acids methyl esters. Report the results indicating two digits after decimal point. Relative standard deviation between the replicates should not exceed 5%.

The following Example is a representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is noted that features of certain embodiments of the invention which are described in detail in the context of one aspect of the invention, may be applicable in other aspects of the invention.

The invention will now be exemplified in the following description of experiments that are carried out in accordance with the invention. It is to be understood that these examples are intended to be in the nature of illustration rather than of limitation. Many modifications and variations of these examples are possible in light of the above teaching. It is therefore, to be understood that within the scope of the appended claims, the invention may be practiced otherwise, in a myriad of possible ways, than as specifically described herein below.

EXAMPLES

Example 1. Production of a Preparation According to the Invention

Lipid preparations were prepared as follows: marine lecithin produced by an extraction process from biomass derived from krill was dissolved in organic solvents and allowed to react with an aqueous solution containing L-serine, $CaCl_2$, phospholipase D (PLD), and acetate buffer. Following the trans-phosphatidylation reaction, the resulting mixture was purified by removal of the water phase, evaporation of the organic solvents, and further purification stages. The resulting powder mainly contained EPA, Palmitic acid, DHA, oleic acid, and linoleic acid bound to phosphatidylserine.

Example 2. Effect of a Preparation According to the Invention on REM Sleep in Patients with Sleep Disorder Study design: The effect of the phospholipid preparation on patients with sleep disorder was evaluated in 14 individuals who were diagnosed with sleep disorders. The diagnosis was obtained through an interview as well as based on measurements obtained by sleep recording in a sleep laboratory (polysomnogram). In certain cases the diagnosis was corroborated by valid sleep questionnaires.

All subjects were recorded for one night in a sleep laboratory. The percentage of REM sleep was calculated as the amount of time spent in REM divided by the entire Total Sleep Time (TST). The percentage of improvement in REM sleep was calculated as $$\frac{(\text{precentage of } REM \text{ at endpoint} - \text{precentage of } REM \text{ at baseline})}{\text{precentage of } REM \text{ at baseline}} * 100.$$

Patients received 2-4 capsules a day (see capsule's ingredients in Table 1), for different durations (21-427 days). The treatment dose and duration and the effect of the preparation on the percentage of REM sleep are described in Table 2.

TABLE 1 list of ingredients in one capsule (167 mg per capsule) containing a preparation of the invention

| Parameter | Specification |
| --- | --- |
| Phophatidylserine | n.l.t. 75 mg/capsule |
| Phosphatidic acid | n.l.t. 13 mg/capsule |
| Lysophosphatidic acid | n.l.t. 2 mg/capsule |
| Total EPA | n.l.t. 21.5 mg/capsule |
| Total Palmitic acid | n.l.t. 16.5 mg/capsule |
| Total DHA | n.l.t. 8.5 mg/capsule |
| Total Oleic acid | n.l.t. 3.5 mg/capsule |
| Total Linoleic acid | n.l.t. 1 mg/capsule |
| Weight percentage of phosphatidylserine (PS) with respect to the preparation | 40-48% |
| Percentage of EPA attached to the PS with respect to all fatty acids attached to the PS | 27-34% |
| Percentage of Palmitic acid attached to the PS with respect to all fatty acids attached to the PS | 21-26% |
| Percentage of DHA attached to the PS with respect to all fatty acids attached to the PS | 12-17% |
| Percentage of Oleic acid attached to the PS with respect to all fatty acids attached to the PS | 5-8% |
| Percentage of Linoleic acid attached to the PS with respect to all fatty acids attached to the PS | 1.2% | n.l.t = not less than

TABLE 2

The effect of the lipid preparation on % of REM sleep

| Patient # | No. of capsules | Duration of administration of the lipids preparations (Days) | % REM at Baseline | % REM at Endpoint | % REM improvement |
| --- | --- | --- | --- | --- | --- |
| 1 | 2* | 56 | 11.6 | 18.3 | 57.8 |
| 2 | 2 | 28 | 15.5 | 25.6 | 65.2 |
| 3 | 2* | 56 | 1 | 23.7 | 2270.0 |
| 4 | 2 | 21 | 1 | 18.3 | 1730.0 |
| 5 | 2 | 42 | 12.3 | 22.8 | 85.4 |
| 6 | 2 | 42 | 19.5 | 26.1 | 33.8 |
| 7 | 2 | 28 | 12.1 | 26.1 | 115.7 |
| 8 | 2 | 56 | 21.8 | 29.2 | 33.9 |
| 9 | 2 | 28 | 9.6 | 21.2 | 120.8 |
| 10 | 2* | 42 | 1 | 18.4 | 1740.0 |
| 11 | 2 | 22 | 19.9 | 11.5 | -42.2 |
| 12 | 2 | 427 | 1.4 | 13.2 | 842.9 |
| 13 | 2 | 137 | 26.5 | 21.7 | -18.1 |
| 14 | 2 | 28 | 19.2 | 25.3 | 31.8 |

*Started with 2 capsules and switched to 4 capsules

Results: In general, as demonstrated in Table 2, 12 out of the 14 patients evaluated in the study demonstrated an increase in the percentage of REM sleep following the administration of the preparation during the study period. The increase in REM sleep varied significantly between patients and the lowest increase was 31.8% of improvement while the highest increase was 2270%. Mean REM improvement was 505%. Out of the 12 patients who were improved, 9 experienced a dramatic improvement that exceeded 35%.

Of note, a poor sleep quality is characterized by a % of REM below 25%. Interestingly out of the 12 cases that had experienced an increase in their REM score, in 5 cases the endpoint measurement of the REM was above 25%.

Example 3. Effect of the Preparation of the Invention on Symptoms of Fatigue in Patients with Sleep Disorder Study design: The effect of the phospholipid preparation on patients with sleep disorders was evaluated in 59 participants between 9-72 years of age. Most of the participants were also diagnosed with ADHD and the majority of those diagnosed with ADHD were on ADHD medications. Out of 59 participants, only 9 were on a treatment regime which included non-stimulant medications and 2 had missing data regarding their medication regime. The baseline characteristics of the participants are described in table 3.

All patients received 2-4 capsules a day (see capsule's ingredients in Table 1) for different duration (8-435 days). The effect of the lipid preparation on symptoms of fatigue was evaluated by using fatigue assessment scale (FAS). FAS is a 10-item scale evaluating symptoms of chronic fatigue and is an acceptable and commonly used scale in various clinical studies evaluating fatigue symptoms. A FAS score below 10 is a marker for sleep disorders.

All subjects filled in the FAS at baseline (prior to the administration of the preparation) and during administration period. A decrease in score represents an improvement in fatigue symptoms, whereas an increase in the score represents deterioration in fatigue symptoms. The effect of the preparation on FAS score are described in Tables 4 and 5.

TABLE 3

Baseline characteristics of the participants

| Characteristic | N = 59 |
| --- | --- |
| Age | Median 19.5 Y (9-72 Y) |
| Gender | F 39% M 61% |
| Sleep Disorders Diagnosis | 59 (100%) |

TABLE 3-continued

Baseline characteristics of the participants

| Characteristic | N = 59 |
|---|---|
| ADHD Diagnosis | 56 (95%) |
| Depression/Mood disorders | 30 (51%) |
| Anxiety disorder | 5 (8.5%) |
| Other Psychiatric conditions | 16 (27%) |
| Other Non-Psychiatric conditions | 9 (15%) |
| ADHD and at least one additional comorbidity | 48 (81.5%) |
| On ADHD Medications | 46 (78%) |
| On Stimulants | 40 (68%) |
| On Non stimulants | 9 (15.5%) |
| On Antidepressants | 22 (17.5%) |
| On Anti-psychotics/Anti-panic/Anti-anxiety medications | 14 (24%) |
| On Anti seizures medications | 14 (24%) |
| On Sleep inducers | 7 (12%) |
| On other medications (Psychiatric or non-Psychiatric) | 6 (10%) |
| At least on one medication | 55/59 (93%) |

Results: Out of the 9 participants that were on non-stimulants medications, 8 were improved in their FAS score (8/9, 88.9%) and 1 participant did not experience a change in his FAS score. Among participants who were not on non-stimulant medications 23 participants (23/48, 47.9%) experienced an improvement in their FAS score, while 25 participants (25/48, 52.1%) did not demonstrated an improvement in their FAS score.

The results suggest that patients on non-stimulant medications might experience a greater improvement in their sleep quality and reduction in fatigue symptoms in comparison with patients who are not treated with non-stimulant medications.

TABLE 4 the effect of the preparation on FAS score in patients on non-stimulants medication Vs patients not on non-stimulants medications

| | PATENTS n (%) | |
|---|---|---|
| FAS SCORE TREND | Not on Non-stimulants N = 48 | On Non-Stimulants N = 9 |
| Improved | 23 (47.9%) | 8 (88.9%) |
| Not improved | 25 (52.1%) | 1 (11.1%) |

TABLE 5

Detailed characteristics and treatment effect on patients consuming non-stimulants medications

| # | On Non-Stimulants | Age | Gender | BMI | Duration of administration of the lipid preparation (Days) | FAS-Mean change from baseline |
|---|---|---|---|---|---|---|
| 16 | Yes | 15 | M | 14.93335 | 213 | -5 |
| 20 | Yes | 21 | M | 26.58106 | 397 | -6 |
| 24 | Yes | 13 | M | 16.46103 | 201 | -3 |
| 25 | Yes | 12 | M | 21.78933 | 92 | -8 |
| 27 | Yes | 12 | F | NA | 15 | -4 |
| 29 | Yes | 11 | M | 28.13142 | 247 | -1 |
| 38 | Yes | 16 | M | 21.03354 | 166 | 0 |
| 51 | Yes | 9 | M | 20.28084 | 107 | -11 |
| 61 | Yes | 17 | M | 19.57755 | 218 | -3 |
| 1 | No | 36 | F | 20.89677 | 147 | -14 |
| 4 | No | 42 | F | 25.68531 | 126 | -2 |
| 5 | No | 17 | M | 25.47216 | 28 | -3 |
| 6 | No | 29 | F | 21.45596 | 193 | -2 |
| 7 | No | 13 | M | 20.2205 | 153 | -5 |
| 8 | No | 45 | F | 29.97753 | 99 | 8 |
| 10 | No | 14 | M | 17.16773 | 8 | -3 |
| 11 | No | 22 | M | 24.40728 | 216 | 5 |
| 12 | No | 15 | M | 19.76621 | 85 | 2 |
| 14 | No | 50 | M | 24.53947 | 203 | -5 |
| 15 | No | 9 | M | 14.62384 | 268 | -3 |
| 17 | No | 53 | F | 36.668 | 266 | 9 |
| 18 | No | 10 | M | 19.72499 | 10 | 6 |
| 21 | No | 19 | M | 21.37904 | 97 | 8 |
| 22 | No | 30 | M | 27.99617 | 203 | 0 |
| 23 | No | 26 | M | 17.97474 | 56 | -7 |
| 26 | No | 15 | F | 19.20454 | 82 | 5 |
| 28 | No | 40 | F | 23.26331 | 209 | 1 |
| 30 | No | 17 | F | 19.52969 | 210 | 1 |
| 31 | No | 14 | M | NA | 95 | -7 |
| 32 | No | 34 | M | 32.3235 | 202 | -4 |
| 33 | No | 15 | M | NA | 329 | 4 |
| 34 | No | 43 | F | 26.60836 | 193 | -1 |
| 35 | No | 26 | M | 23.49306 | 379 | 2 |
| 37 | No | 36 | M | 28.79615 | 216 | 6 |
| 39 | No | 15 | M | 18.79445 | 138 | -1 |
| 41 | No | 62 | F | 37.18712 | 426 | 2 |
| 42 | No | 11 | M | 21.07967 | 288 | 6 |
| 43 | No | 38 | F | 25.69502 | 272 | 1 |
| 45 | No | 17 | F | 24.79961 | 373 | 4 |
| 46 | No | 22 | M | 21.69966 | 253 | -8 |
| 47 | No | 27 | M | 37.3057 | 34 | -8 |
| 49 | No | 29 | M | 31.7496 | 101 | 11 |
| 50 | No | 25 | F | 21.14375 | 314 | 0 |
| 52 | No | 19 | M | NA | 435 | 1 |
| 53 | No | 24 | M | 35.15345 | 113 | 2 |
| 54 | No | 16 | F | 21.41252 | 103 | -9 |
| 55 | No | 20 | M | 23.86963 | 217 | 1 |
| 56 | No | 36 | F | 26.00017 | 255 | -5 |
| 57 | No | 10 | M | 22.81457 | 311 | 6 |
| 58 | No | 42 | F | 28.32187 | 147 | -10 |
| 59 | No | 22 | M | 30.89659 | 323 | -13 |
| 62 | No | 40 | F | 25.33103 | 202 | 3 |
| 63 | No | 40 | F | 29.45402 | 29 | -2 |
| 64 | No | 16 | M | 30.89659 | 285 | -9 |
| 65 | No | 13 | F | 19.08605 | 196 | 2 |
| 66 | No | 72 | F | 29.1212 | 34 | -7 |
| 68 | No | 11 | F | 27.89956 | 35 | -2 |

The invention claimed is:

1. A method for one or both of improving sleep in a subject and treating at least one sleep problem in a subject, the method comprising administering a preparation comprising an effective amount of long chain poly unsaturated fatty acids (LC-PUFA) attached to phosphatidylserine (PS); wherein
    the weight percentage of the PS with respect to the preparation is greater than about 8%,
    the content of LC-PUFA attached to the PS in the preparation out of the total fatty acids content attached to the PS in the preparation is greater than about 10%,
    the content of EPA attached to the PS in the preparation out of the total fatty acids content attached to the PS in the preparation is greater than about 5%,
    the content of Palmitic acid attached to the PS in the preparation out of the total fatty acids content attached to the PS in the preparation is greater than 14% and lower than 42%, the content of Docosahexaenoic acid (DHA) attached to the PS in the preparation out of the total fatty acids content attached to the PS in the preparation is greater than about 6% and lower than about 25%, the content of Oleic acid attached to the PS in the preparation out of the total fatty acids content attached to the PS in the preparation is greater than 1% and lower than 15%, and the content of Linoleic acid attached to the PS in the preparation out of the total fatty acids content attached to the PS in the preparation is greater than about 0.1% and lower than about 6%;

wherein the sleep problem comprises insufficient REM sleep; and wherein improving sleep comprises improving REM sleep.

2. The method according to claim 1, wherein a weight percentage of the PS with respect to the preparation is greater than about 20%.

3. The method according to claim 2, wherein a weight percentage of the PS with respect to the preparation is greater than about 40%.

4. The method according to claim 1, wherein the content of LC-PUFA attached to the PS in the preparation out of the total fatty acids content attached to the PS in the preparation is greater than about 20%.

5. The method according to claim 4, wherein the content of LC-PUFA attached to the PS in the preparation out of the total fatty acids content attached to the PS in the preparation is greater than about 40%.

6. The method according to claim 1, wherein the content of EPA attached to the PS in the preparation out of the total fatty acids content attached to the PS in the preparation is greater than about 10%.

7. The method of claim 6, wherein the content of EPA attached to the PS in the preparation out of the total fatty acids content attached to the PS in the preparation is greater than about 25%.

8. The method according to claim 1, wherein the content of Palmitic acid attached to the PS in the preparation out of the total fatty acids content attached to the PS in the preparation is greater than about 20% and lower than about 30%.

9. The method of claim 8, wherein the content of Palmitic acid attached to the PS in the preparation out of the total fatty acids content attached to the PS in the preparation is greater than 21% and lower than 26%.

10. The method according to claim 1, wherein the content of Docosahexaenoic acid (DHA) attached to the PS in the preparation out of the total fatty acids content attached to the PS in the preparation is greater than about 8% and lower than about 22%.

11. The method according to claim 1, wherein the content of Oleic acid attached to the PS in the preparation out of the total fatty acids content attached to the PS in the preparation is greater than about 2% and lower than about 13%.

12. The method according to claim 1, wherein the content of Linoleic acid attached to the PS in the preparation out of the total fatty acids content attached to the PS in the preparation is greater than about 0.5% and lower than about 4.0%.

13. The method according to claim 1, wherein said method reduces fatigue symptoms.

14. The method according to claim 1, wherein said subject is suffering from fatigue or insufficient sleep duration.

15. The method of claim 1, wherein the subject suffers from ADHD symptoms.

16. The method of claim 15, wherein the subject is being treated with non-stimulant medications for the treatment of ADHD.

17. The method of claim 1, wherein the subject suffers from Autism.

18. The method of claim 1, wherein the subject suffers from Epilepsy.

19. A preparation comprising an effective amount of a long chain poly unsaturated fatty acids (LC-PUFA) attached to phosphatidylserine (PS), wherein the weight percentage of the PS with respect to the preparation is greater than about 40%, wherein the content of LC-PUFA attached to the PS in the preparation out of the total fatty acids content attached to the PS in the preparation is greater than about 40%, wherein the content of EPA attached to the PS in the preparation out of the total fatty acids content attached to the PS in the preparation is greater than about 25%, wherein the content of Palmitic acid attached to the PS in the preparation out of the total fatty acids content attached to the PS in the preparation is greater than 21% and lower than 26%, wherein the content of Docosahexaenoic acid (DHA) attached to the PS in the preparation out of the total fatty acids content attached to the PS in the preparation is greater than about 12% and lower than about 17%, wherein the content of Oleic acid attached to the PS in the preparation out of the total fatty acids content attached to the PS in the preparation is greater than 5% and lower than 8% and wherein the content of Linoleic acid attached to the PS in the preparation out of the total fatty acids content attached to the PS in the preparation is greater than about 1% and lower than about 2%.

* * * * *